(12) United States Patent
Pashley et al.

(10) Patent No.: US 11,198,074 B2
(45) Date of Patent: Dec. 14, 2021

(54) METHOD FOR ASSISTING THERMALLY-INDUCED CHANGES

(71) Applicant: NEWSOUTH INNOVATIONS PTY LIMITED, Sydney (AU)

(72) Inventors: Richard Pashley, Canberra (AU); Xinkai Xue, Harrison (AU); Chao Fan, Hackett (AU); Barry Ninham, Cook (AU); Muhammad Shahid, Curtin (AU)

(73) Assignee: NEWSOUTH INNOVATIONS PTY LIMITED, Sydney (AU)

( * ) Notice: Subject to any disclaimer, the term of this patent is extended or adjusted under 35 U.S.C. 154(b) by 40 days.

(21) Appl. No.: 15/577,013

(22) PCT Filed: May 27, 2016

(86) PCT No.: PCT/AU2016/050416
§ 371 (c)(1),
(2) Date: Nov. 27, 2017

(87) PCT Pub. No.: WO2016/187674
PCT Pub. Date: Dec. 1, 2016

(65) Prior Publication Data
US 2018/0154279 A1   Jun. 7, 2018

(30) Foreign Application Priority Data

May 27, 2015 (AU) ............................... 2015 901956

(51) Int. Cl.
C02F 1/02 (2006.01)
C02F 1/10 (2006.01)
(Continued)

(52) U.S. Cl.
CPC ............... B01D 3/346 (2013.01); B01D 1/14 (2013.01); B01D 3/009 (2013.01); C02F 1/02 (2013.01); C12M 1/04 (2013.01); C02F 1/10 (2013.01)

(58) Field of Classification Search
CPC .... C02F 1/02; C02F 1/025; C02F 1/04; C02F 1/10; C01D 5/06; C01D 5/00–18;
(Continued)

(56) References Cited

U.S. PATENT DOCUMENTS 2,334,563 A * 11/1943 Lavine ................ B01D 9/0031
159/16.2
3,840,002 A   10/1974 Douglas et al.
(Continued)

FOREIGN PATENT DOCUMENTS

BE        856467 A    10/1977
CN      1073924 A     7/1993
(Continued)

OTHER PUBLICATIONS

Guthrie et al., "Decompositon of Alkali Chlroides at High Temperatures", Mar. 26, 1931, Avialable online at: https://pubs.rsc.org/-/content/articlepdf/1931/tf/tf9312700228 (Year: 1931).*
(Continued)

*Primary Examiner* — Jonathan Luke Pilcher
(74) *Attorney, Agent, or Firm* — Ballard Spahr LLP

(57) ABSTRACT

Disclosed herein is a method for assisting a thermally-induced change to a nano-sized solute or dispersed-phase in a liquid. The method comprises the step of passing gas bubbles through the liquid, the gas in the gas bubbles having a temperature higher than the bulk temperature of the liquid.

23 Claims, 12 Drawing Sheets

(51) Int. Cl.
  *B01D 1/14* (2006.01)
  *B01D 3/34* (2006.01)
  *C12M 1/04* (2006.01)
  *B01D 3/00* (2006.01)

(58) Field of Classification Search
  CPC ...... B01D 1/0041; B01D 1/0058; B01D 1/14; B01F 3/04099–04439; B01F 2003/04127–04234
  USPC ................................................ 159/16.1, 16.2
  See application file for complete search history.

(56) References Cited

U.S. PATENT DOCUMENTS

| | | | |
|---|---|---|---|
| 4,685,444 | A | 8/1987 | Durrenberger |
| 5,335,588 | A | 8/1994 | Mahlich |
| 6,265,623 | B1 | 7/2001 | Morawietz et al. |
| 6,605,750 | B1 | 8/2003 | Bessho et al. |
| 2003/0019789 | A1 | 1/2003 | Kwak |
| 2003/0180283 | A1 | 9/2003 | Batycky et al. |
| 2004/0040671 | A1 | 3/2004 | Duesel et al. |
| 2011/0112203 | A1 | 5/2011 | Steiner et al. |
| 2011/0203994 | A1* | 8/2011 | McGinnis ............ B01D 61/005 210/650 |

FOREIGN PATENT DOCUMENTS

| | | |
|---|---|---|
| CN | 103539157 A | 1/2014 |
| DE | 2611454 A1 | 9/1977 |
| GB | 1471195 A | 4/1977 |
| GB | 2198049 A | 6/1988 |
| JP | S5760188 A | 4/1982 |
| JP | H1033943 A | 2/1998 |
| JP | 2000-051850 A | 2/2000 |
| JP | 2005-270857 A | 10/2005 |
| JP | 2012-223746 A | 11/2012 |
| KR | 10-2008-0012499 A | 2/2008 |
| RU | 2464088 C1 | 10/2012 |
| WO | WO 2016/187674 | 12/2016 |

OTHER PUBLICATIONS

McGinnis et al., "Energy requirements of ammonia-carbon dioxide forward osmosis desalination", Mar. 10, 2007, Desalination, vol. 207, Issues 1-3, pp. 370-382. (Year: 2007).*

Helen K. Roobottom, H. Donald B. Jenkins, Jack Passmore, and Leslie Glasser Journal of Chemical Education 1999 76 (11), 1570 DOI: 10.1021/ed076p1570 (Year: 1999).*

Christine L. Henry and Vincent S. J. Craig Langmuir 2009 25 (19), 11406-11412 DOI: 10.1021/la9015355 (Year: 2009).*

Lewis et al., "Sulfate Minerals: A Problem for the Detection of Organic Compounds on Mars?",Astrobiology, vol. 15, No. 3, 2015, DOI: 10.1089/ast.2014.1160 (Year: 2015).*

Thomas, "Thermal Decomposition of Sodium Carbonate Solutions", Journal of Chemical and Engineering Data, vol. 8, No. 1, Jan. 1963, pp. 51-54 (Year: 1963).*

Haby, Jeff, "What is Dry Air", TheWeatherPrediction.com, Mar. 17, 2006 (date obtained via WayBack Machine), URL: https://www.theweatherprediction.com/habyhints2/455/ (Year: 2006).*

International Preliminary Report on Patentability dated Nov. 28, 2017 by the International Searching Authority for International Patent Application No. PCT/AU2016/050416, which was filed on May 27, 2016 and published as WO 2016/187674 on Dec. 1, 2016 (Applicant—NewSouth Innovations PTY Limited) (6 pages).

Extended European Search Report dated Nov. 20, 2018 by the European Patent Office for Patent Application No. 16798964.9, which was filed on May 27, 2016 and published as EP 3303963 on Apr. 11, 2018 (Inventor—Pashley et al.; Applicant—NewSouth Innovations Pty, Ltd.) (9 pages).

PCT/AU2016/050416 (WO 2016/187674), May 27, 2016 (Dec. 1, 2016), NewSouth Innovations PTY Limited.

International Search Report and Written Opinion dated Jul. 4, 2016 by the International Searching Authority for International Patent Application No. PCT/AU2016/050416, which was filed on May 27, 2016 and published as WO 2016/187674 on Dec. 1, 2016 (Applicant—NewSouth Innovations PTY Limited) (9 pages).

Shahid, M., et al., "Study of a Novel Method for the Thermolysis of Solutes in Aqueous Solution Using a Low Temperature Bubble Column Evaporator", J. Phys. Chem. B.; 119(25):8072-9, (2015).

Xue, X., et al., "A study of low temperature inactivation of fecal coliforms in electrolyte solutions using hot air bubbles", Desalination and Water Treatment, 57(20), pp. 9444-9454, (2016) (Published online Mar. 27, 2015).

Craig, V. et al., Effect of Electrolytes on Bubble Coalescence. Nature. 1993; 364:317-9.

Fan, C. et al., Studies on Bubble Column Evaporation in Various Salt Solutions. J Solution Chem. 2014; 43:1297-312.

Francis, M.J. and Pashley, R.M., Application of a Bubble Column for Evaporative Cooling and a Simple Procedure for Determining the Latent Heat of Vaporization of Aqueous Salt Solutions. J Phys Chem B. 2009; 113:9311-5.

Francis, M.J. and Pashley, R.M., Thermal Desalination Using a Non-Boiling Bubble Column. Desalin Water Treat. 2009; 12:155-61.

Fulks, G. et al., A Review of Solid Materials as Alternative Ammonia Sources for Lean NOx Redution with SCR. SAE Technical Paper (2009) (13 pages).

Gokel, G.W., Dean's Handbook of Organic Chemistry. McGraw-Hill, New York: 2004; 2nd Ed., pp. 2.4-2.5 (39 pages).

How, Y. et al., Performance of Forward (Direct) Osmosis Process: Membrane Structure and Transport Phenomenon. Environ Sci Technol. 2006; 40:2408-13.

Kolthoff, I. and Miller, I., The Chemistry of Persulfate. I. The Kinetics and Mechanism of the Decomposition of the Persulfate Ion in Aqueous Medium. J Am Chem Soc. 1951: 73:3055-9.

Shadid, M. and Pashley, R.M., A Study of the Bubble Column Evaporator Method for Thermal Desalination. Desalination. 2014; 351:236-42.

Shadid, M. et al., Study of a Novel Method for the Thermolysis of Solutes in Aqueous Solution Using a Low Temperature Bubble Column Evaporator. J Phys Chem B. 2015; 119(25):8072-9.

Shadid, M. et al., Use of the High Density, Low Temperature, Bubble Column for Thermally Efficient Water Sterilization. Desalin Water Treat. 2013; pp. 1-9.

Shadid, M., A Study of the Bubble Column Evaporator Method for Improved Sterilization. J Water Process Eng. 2015; 8:e1-6.

* cited by examiner

METHOD FOR ASSISTING THERMALLY-INDUCED CHANGES

CROSS REFERENCE TO RELATED APPLICATIONS

This application is a U.S. National Phase Application of International Application No. PCT/AU2016/050416, filed May 27, 2016, which claims priority to AU 2015901956, filed May 27, 2015, both of which applications are hereby incorporated by reference in their entireties.

TECHNICAL FIELD

The present invention relates to a method for assisting thermally-induced changes to a solute or dispersed phase in a liquid, such as an aqueous solution.

BACKGROUND

Concentrated aqueous solutions of certain salts inhibit bubble coalescence in the solution, compared to bubbles in non-saline water. This phenomenon is known as bubble coalescence inhibition and allows control of bubble size. Coalescence inhibited bubbles in such solutions are of smaller average size when compared to bubbles in non-saline water.

While several attempts have been made to explain bubble coalescence inhibition, it is still not completely understood. While there is still no explanation for the occurrence of bubble coalescence inhibition, the combination of coalescence-inhibited bubbles and the rapid uptake of water vapor into the bubbles facilitates the design of bubble column evaporators (BCEs) for highly efficient heat transfer and rapid water vapor capture. For example, BCEs can be used to capture water vapor in a desalination process as described in Shahid, M.; Pashley, R. M., A Study of the Bubble Column Evaporator Method for Thermal Desalination. *Desalination* 2014, 351, 236-242.

Many substances undergo chemical or physical changes when heated. For example, on heating, many substances will undergo chemical reactions. Thermally-induced chemical or physical changes have a variety of industrial applications. For example, the thermal decomposition of ammonium bicarbonate ($NH_4HCO_3$) in aqueous solution is an important and energy intensive process in the application of forward osmosis and more recently in the regeneration of ion exchange resins. In aqueous solutions potassium persulfate ($K_2S_2O_8$) is often used as a radical initiator for the process of emulsion polymerization. Persulfates are among the most powerful and useful oxidizing agents and sodium and potassium persulfate salts are mostly used. However, the persulfates decomposition generally requires high activation energy and is relatively slow at room temperature and therefore direct bulk solution heating is used to speed up the decomposition process.

When a substance is dissolved or dispersed in a liquid, a thermally-induced chemical or physical change to the substance may be effected by heating the bulk liquid to a temperature effective to thermally-induce the chemical or physical change. However, this can be an energy intensive process as it requires raising the bulk temperature of the liquid.

It would be advantageous to provide an alternative method for inducing or accelerating thermally-induced chemical or physical changes to a substance dissolved or dispersed in a liquid.

SUMMARY OF THE INVENTION

In a first aspect, the present invention provides a method for assisting a thermally-induced change to a nano-sized solute or dispersed phase in a liquid, the method comprising the step of:
  passing gas bubbles through the liquid, the gas in the gas bubbles having a temperature higher than the bulk temperature of the liquid.

Preferably, the liquid is water or an aqueous solution.

In one embodiment, the bulk temperature of the liquid is less than the temperature which would cause the thermally-induced change to the nano-sized solute or dispersed-phase.

In one embodiment, the nano-sized solute or dispersed-phase has a diameter of less than 500 nm, e.g. a diameter in the range of 0.5 nm to 200 nm.

In one embodiment, the bubbles have a diameter of 0.1 mm to 7 mm, e.g. 1 mm to 3 mm.

In one embodiment, the nano-sized solute or dispersed-phase is selected from the group consisting of thermally decomposable inorganic solutes, thermally decomposable organic solutes, enzymes, antibiotics and hormones.

In one embodiment, the liquid is an aqueous solution, and the aqueous solution comprises a bubble coalescence inhibitor. The bubble coalescence inhibitor may, for example, be selected from the group consisting of NaCl, $CaCl_2$, sucrose, emulsifiers and surfactants.

In one embodiment, the gas is selected from the group consisting of dry air, humidified air, carbon dioxide, nitrogen, helium, argon and oxygen.

BRIEF DESCRIPTION OF THE FIGURES

The invention will be further described, by way of example only, with reference to the accompanying drawings, in which.

DESCRIPTION OF THE INVENTION

Figure 1:
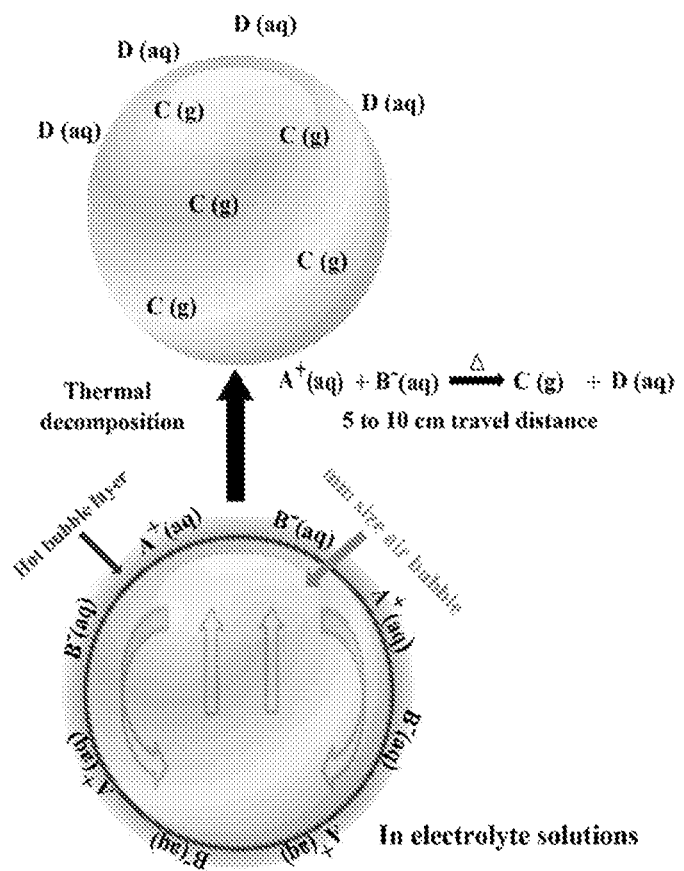
FIG. 1 shows a schematic diagram of the thermal decomposition of nano-sized solutes ($A^+_{(aq)}$ and $B^-_{(aq)}$ to $C_{(g)}$ and $D_{(aq)}$) according to the method of the present invention using a hot air bubble layer.

The inventors have found a method that can be used to assist a thermally-induced change to a nano-sized solute or dispersed phase in a liquid.

In a first aspect, the present invention provides a method for assisting a thermally-induced change to a nano-sized solute or dispersed phase in a liquid. The method comprises the step of passing gas bubbles through the liquid. In the method of the invention, the gas in the gas bubbles has a temperature higher than the bulk temperature of the liquid.

A dispersion comprises a dispersed phase in a continuous phase. The method of the present invention can be applied to any dispersion comprising a nano-sized dispersed phase in a liquid. The dispersed phase may, for example, be a solid, a liquid, or a micelle. A solid dispersed in a liquid may be in the form of a suspension. A liquid dispersed in another liquid may be in the form of an emulsion.

The thermally-induced change may be a chemical reaction or physical change to the solute or dispersed phase. A thermally-induced chemical reaction may involve a reaction between the solute or dispersed phase and one or more other components present in the liquid, e.g. a reaction with the liquid and/or with one or more solutes dissolved in the liquid.

As used herein, the term "assisting a thermally-induced change" encompasses inducing a thermally-induced change; the term "assisting a thermally-induced change" also encompasses increasing the rate of a thermally-induced change i.e. the thermally-induced change occurs at a faster rate than would occur otherwise.

The liquid may be aqueous or non-aqueous. Preferably, the liquid is a liquid that has a high heat of evaporation, such as water or an aqueous solution. The heat of evaporation (also referred to as the enthalpy of vaporization or the heat of vaporization) is the enthalpy change required to transform a given quantity of a substance from a liquid into a gas at a given pressure. For a liquid having a high heat of evaporation, more heat is required to vaporize a given quantity of the liquid than a liquid having a lower heat of vaporization. In the method of the present invention, a liquid having a high heat of evaporation is preferred as the passing of the gas through the liquid will generally cause less heating of the bulk liquid (as a result of the vapour captured by the gas bubbles) compared to a liquid having a lower heat of evaporation. More preferably, the liquid is water or an aqueous solution, as bubble coalescence inhibition can be used to control the size of bubbles in such liquids.

The term "aqueous solution" refers to a solution in which water is the only solvent or is at least 50% by weight of the total solvents in the solution. An aqueous solution may be part of an emulsion or microemulsion, such as the aqueous component of an oil/water emulsion or microemulsion. An aqueous solution may comprise water and a water co-miscible solvent, such as methanol or ethanol, provided that water comprises at least 50% by weight of the solvents present.

As used herein, the term "nano-sized solute or dispersed phase" refers to a solute or dispersed phase having a maximum dimension of less than 500 nm, that is, the maximum dimension in any direction is less than 500 nm. The nano-sized solute or dispersed phase typically has a maximum dimension in the range of 0.1 to 500 nm, e.g. 0.1 to 250 nm, 0.1 nm to 50 nm, 0.5 to 250 nm, 0.5 to 200 nm or 0.5 to 50 nm. For a nano-sized solute or dispersed phase that is approximately spherical in shape, the diameter of the nano-sized solute or dispersed phase is less than 500 nm. Typically, the nano-sized solute or dispersed phase has a diameter of less than 250 nm, e.g. less than 150 nm, e.g. less than 50 nm. The nano-sized solute or dispersed phase may, for example, have a diameter of between 0.1 to 250 nm, 0.5 to 250 nm, 0.5 to 200 nm, 0.5 to 50 nm or 0.5 to 5 nm. As used herein, the term "nano-sized solute or dispersed phase" encompasses solutes or dispersed phases having a maximum dimension of less than 1 nm.

The inactivation of fecal coliforms using a BCE has recently been described by Xue et al [Xue, X.; Pashley, R. M., A Study of Low Temperature Inactivation of Fecal Coliforms in Electrolyte Solutions Using Hot Air Bubbles. *Desalin. Water Treat.* 2015, 1-11]. Fecal coliforms are bacteria and typically have a dimension of about 0.5-2 μm. The BCE process was used to inactivate coliforms in solution while maintaining a relatively low column solution temperature. Nano-sized solutes and dispersed phases differ significantly from the relatively large bacteria inactivated by the process described in Xue et al.

Coliform bacteria comprise a cellular membrane. The inventors now believe that the inactivation of the fecal coliforms in the process described in Xue et al is due to continuous collisions between the small, heated air bubbles and the cellular membranes of the coliform bacteria. Thus, Xue et al discloses a process in which the fecal coliforms are inactivated and made no longer viable through changes to the cell's membrane.

The inventors have now found a method that can be used to assist thermally-induced changes to nano-sized solutes and dispersed phases that do not comprise a cell membrane, such as thermally decomposable inorganic solutes, thermally decomposable organic solutes, proteins, enzymes, antibiotics and hormones.

The nano-sized solute or dispersed phase may be a solute or dispersed phase that, in the liquid, is capable of undergoing a thermally-induced chemical or physical change at a temperature of less than 1000° C., e.g. less than 600° C. or less than 500° C. In some embodiments, the nano-sized solute or dispersed phase is one that undergoes a thermally-induced chemical or physical change at a temperature below 250° C., e.g. below 200° C., below 150° C., below 100° C. or below 80° C. In some embodiments, the nano-sized solute or dispersed phase is one that undergoes a thermally-induced chemical or physical change at a temperature in the range of 40° C. to 80° C. In some embodiments, the nano-sized solute or dispersed phase is one that undergoes a thermally-induced chemical or physical change at a temperature below the boiling point of the liquid.

The nano-sized solute may, for example, be a thermally decomposable inorganic solute or a thermally decomposable organic solute. The thermally decomposable inorganic solute may be an ion of an inorganic or organic salt. The ion may be, for example, an acetate, persulfate, ammonium, bicarbonate, peroxide and carbonate.

The nano-sized solute may be a thermally decomposable organic solute, such as urea and acetic acid.

The nano-sized solute or dispersed phase may be an enzyme or protein. The enzyme may be any enzyme. For example, the enzyme may be a thermally labile enzyme.

The nano-sized solute or dispersed phase may be an antibiotic or a hormone.

The thermally-induced chemical or physical change may be thermal decomposition. Thermal decomposition is a chemical decomposition caused by heat. The decomposition temperature of a substance is the temperature at which the substance chemically decomposes. For example, ammonium bicarbonate ($NH_4HCO_3$), as a solid or dissolved in water or an aqueous solution, will thermally decompose into ammonia gas, carbon dioxide and water.

When the nano-sized solute is an enzyme, the thermally induced change may be the denaturation or inactivation of the enzyme.

When the nano-sized solute is an antibiotic or hormone, the thermally induced change may alter, or decompose, the chemical structure of the antibiotic or hormone which will in turn have an impact on the biological activity of the antibiotic or hormone.

Accordingly, in an aspect, the present invention provides a method for assisting a thermal-decomposition of a nano-sized solute or dispersed phase in a liquid, the method comprising the step of passing gas bubbles through the liquid, the gas in the gas bubbles having a temperature higher than the bulk temperature of the liquid.

In an embodiment, the present invention provides a method for inducing, or increasing the rate of, thermal decomposition of a nano-sized solute or dispersed phase in a liquid, the method comprising the step of passing gas bubbles through the liquid, the gas in the gas bubbles having a temperature higher than the bulk temperature of the liquid.

In another aspect, the present invention provides a method for denaturing or inactivating an enzyme in a liquid, the method comprising the step of passing gas bubbles through the liquid, the gas in the gas bubbles having a temperature higher than the bulk temperature of the liquid.

In another aspect, the present invention provides a method for altering, or decomposing, the chemical structure of an antibiotic or hormone in a liquid, the method comprising the step of passing gas bubbles through the liquid, the gas in the gas bubbles having a temperature higher than the bulk temperature of the liquid.

The bubbles may be passed through the liquid in either a continuous or an intermittent manner. Preferably, the bubbles are passed through the liquid in a continuous stream.

As the gas bubbles are introduced and passed though the liquid, a transient hot surface layer is produced around each rising bubble. The transient hot surface layer has a higher temperature than the bulk temperature of the liquid. Without wishing to be bound by theory, it is believed that by passing the gas bubbles, where the gas in the gas bubbles has a temperature higher than the bulk temperature of the liquid, through the liquid, a transient hot surface layer is produced around each rising bubble. The inventors believe that, in some embodiments, it is the interaction of the nano-sized solute or dispersed phase with this transient hot surface layer which results in the thermally-induced chemical or physical change to the solute or dispersed phase, even when the bulk temperature of the liquid is below a temperature that will cause the thermally-induced chemical or physical change to the solute or dispersed phase. In other embodiments, particularly for larger solutes or when the dispersed phase is a solid, the inventors believe that the solute or dispersed phase may penetrate the surface of the bubble and come into direct contact with the gas and, in such embodiments, exposure of the nano-sized solute or dispersed phase to the hot gas of the bubble results in the thermally-induced chemical or physical change to the solute or dispersed phase, in addition to any thermally-induced chemical or physical change induced by the transient hot surface layer surrounding the bubble.

FIG. 1 shows a schematic diagram of the decomposition of nano-sized solutes ($A^+_{(aq)}$ and $B^-_{(aq)}$) by contact with the hot surface layer surrounding a hot air bubble in accordance with an embodiment of the method of the invention. Degradable chemicals exposed to this hot layer are decomposed into other products ($C_{(g)}$ and $D_{(aq)}$ in FIG. 1). Gaseous products produced by the decomposition (e.g. $C_{(g)}$ in FIG. 1) can be rapidly captured by the rising bubbles, due to the internal gas/vapour rotational flow within the rising bubbles.

As the gas bubbles pass through the liquid, the transient hot surface layer causes vaporisation of some of the liquid which is picked up by the gas bubble. This results in cooling of the gas bubble as it passes through the liquid and, as the gas bubble passes through the liquid, the temperature and extent of the transient hot surface layer diminishes. As a result of the vaporisation of some of the liquid as the gas bubbles pass through the liquid, the gas bubbles can be passed through the liquid without substantially increasing the bulk temperature of the liquid. The present invention therefore provides a method which can be used to assist thermally-induced chemical or physical changes to solutes and dispersed phases in a liquid that does not require heating the bulk liquid.

Bubble coalescence inhibition is exhibited in water and aqueous solutions, whilst this phenomenon is not observed in non-aqueous liquids and solutions. When the liquid is water or an aqueous solution, bubble coalescence inhibition can advantageously be used to control the size of bubbles in the liquid. This is advantageous at it allows greater control over the method of the invention. Bubbles having a diameter of less than 1 mm are highly spherical, are less able to pick up vapor and move more slowly though a liquid than larger bubbles. Larger bubbles are more readily able to pick up vapor as they pass through a liquid, but have a smaller total surface area for a given volume of gas than smaller bubbles, resulting in less contact between the transient hot surface layer surrounding the bubbles and the nano-sized solute or dispersed phase in the liquid. Bubble coalescence inhibition can be used to control the size of bubbles in water or an aqueous solution thereby allowing greater control over the method of the present invention.

Accordingly, in some embodiments in which the liquid is an aqueous solution, the aqueous solution may comprise a bubble coalescence inhibitor at a concentration sufficient to inhibit bubble coalescence. In some embodiments, the nano-sized solute or dispersed phase may itself be a bubble coalescence inhibitor. In some embodiments in which the liquid is water or an aqueous solution, a bubble coalescence inhibitor is added to the water or aqueous solution prior to passing the bubbles through the water or aqueous solution.

As used herein, the term "bubble coalescence inhibitor" refers to any substance which, when present in an aqueous solution, above a certain concentration, inhibits bubbles in the aqueous solution from coalescence. Any bubble coalescence inhibitor can be used in the method of the invention. A person skilled in the art can readily determine whether a substance is a bubble coalescence inhibitor. For example, a person skilled in the art can determine whether a substance is a bubble coalescence inhibitor by adding the substance at different concentrations to samples of an aqueous solution and visually observing the effect of the substance on the coalescence of bubbles passed through the aqueous solution. Examples of bubble coalescence inhibitors include certain salts e.g. $MgCl_2$, $MgSO_4$, NaCl, NaBr, $NaNO_3$, $Na_2SO_4$, $CaCl_2$, $Ca(NO_3)_2$, KCl, KBr, $KNO_3$, $NH_4Br$, $NH_4NO_3$, CsBr, LiCl, $LiNO_3$, $LiSO_4$, and various sugars, e.g. sucrose. Other bubble coalescence inhibitors include emulsifiers and surfactants. The bubble coalescence inhibitor is typically included in the aqueous solution in an amount sufficient to inhibit bubbles from coalescing in the aqueous solution.

In some embodiments, the bubble coalescence inhibitor is a surfactant or an emulsifier. The surfactant may, for example, be a non-ionic surfactant, a cationic surfactant, an anionic surfactant (e.g. common soap), or a zwitterionic surfactant. Non-ionic surfactants include monododecyl octaethylene glycol. Cationic surfactants include cetylpyridinium chloride. Anionic surfactants include sodium dodecyl sulphate. Examples of emulsifiers include lipids, proteins and fats which act as an emulsifier. Some polymers also act as emulsifiers, such as, for example, sodium carboxymethyl cellulose, methyl cellulose and polyoxyethylene stearate.

When the bubble coalescence inhibitor is a surfactant or an emulsifier, the surfactant or emulsifier forms a coating around the bubbles. For example, when a surfactant is used as the bubble coalescence inhibitor, the surfactant coats the surface of the bubbles. Due to the presence of the surfactant or emulsifier in the surface layer of the bubbles, the boiling point of the surface layer of the bubbles is higher than the surface layer of bubbles formed in the absence of a bubble coalescence inhibitor or formed in the presence of other bubble coalescence inhibitors which do not form a coating around the bubbles. As a result, the transient hot surface layer of the bubbles can reach higher temperatures than in bubbles formed in the absence of a bubble coalescence inhibitor or in the presence of other bubble coalescence inhibitors which do not form a coating around the bubbles. In the absence of such a coating, the inventors believe that the surface layer of the hot bubbles in an aqueous liquid may be limited to about 100° C., because at this temperature, the water around the bubble will boil and cool. For example, using a surfactant or emulsifier as a bubble coalescence inhibitor, the temperature of the transient hot surface layer may reach temperatures of greater than 100° C., e.g. greater than 300° C., e.g. greater than 500° C. Exposure of the nano-sized solute or dispersed phase to transient hot surface layers having such high temperatures increases the effectiveness of the thermal transfer and, in turn enhance the effectiveness of any thermally-induced chemical or physical change induced by the transient hot surface layer surrounding the bubble on the nano-sized solute or dispersed phase. Thus, when the bubble coalescence inhibitor is a surfactant or an emulsifier, the surfactant or emulsifier serves to control the bubble size and may also enhance the effectiveness of the method of the invention.

The gas bubbles used in the method of the invention may be produced by, for example, using a bubble column evaporator. Small air bubbles in water rise under buoyancy forces in a fairly regular and easily predicted manner. They follow Stokes law up to radii of about 0.5 mm. However, larger bubbles (more than 0.5 mm radii) exhibit more complex behaviour. Bubbles with radii above about 1-2 mm, rise at a limited rate of only about 25 cm/sec. in water. This behaviour is not predicted by Stokes law. The situation arises because the rising larger air bubbles become non-spherical and oscillate both in shape and vertical trajectory. Then they combine with the internal gas/vapour rotational flow within the rising bubble due to shear forces at the oscillating bubble boundary created by the passing water flow. This results in a more rapid water vapour equilibration time, of a few tenths of a second, rather than several seconds expected from Fick's law for quiescent water vapour diffusion.

As mentioned above, the gas bubbles used in the method of the invention may be produced by, for example, using a bubble column evaporator. In the presence of a surfactant or emulsifier bubble coalescence inhibitor in the liquid, the bubbles are coated with the surfactant or emulsifier. This occurs instantaneously as the bubbles are formed at the sinter.

In some embodiments, the bubbles have a diameter range of 0.1 to 7 mm, e.g. 0.1 to 5 mm. In some embodiments, the bubbles have a diameter in the range of 1 to 3 mm. e.g. 1.5 to 2.5 mm. When the liquid is water or aqueous solution, a bubble coalescence inhibitor can be used to control the bubble size such that all or most of the bubbles have a diameter in the range of 0.1 to 7 mm, e.g. in the range of 0.1 to 5 mm or 1 to 3 mm.

In the method of the invention, the gas in the gas bubbles has a higher temperature than the bulk temperature of the liquid. In some embodiments, the bulk temperature of the liquid is less than a temperature that would induce a thermally-induced chemical or physical change to the nano-sized solute or dispersed phase. In other embodiments, the bulk temperature of the liquid is a temperature that is effective to induce a thermally-induced chemical or physical change to the nano-sized solute or dispersed phase; in such embodiments, the method of the invention may be used to more rapidly induce thermally-induced changes to the nano-sized solute or dispersed phase. The bulk temperature of a liquid is the temperature of a liquid away from a surface, e.g. the surface of a container containing the liquid or the surface of a bubble passing through the liquid. In the method of the present invention, the bulk temperature of the liquid can be determined by measuring the temperature of the liquid at a point away from a surface. As the bubbles passing through the liquid in the method of the invention cause rapid mixing of the liquid, the bulk temperature of the liquid can generally be determined by a single measurement of the temperature of the liquid using a conventional thermometer or other apparatus for measuring the temperature of a liquid. A person skilled in the art will be able to select an appropriate method for determining the bulk temperature of a liquid, taking into account such factors as, for example, the method used to pass the bubbles through the solution and the vessel used to contain the solution etc.

M. J. Francis and R. M. Pashley, Application of a bubble column for evaporative cooling and a simple procedure for determining the latent heat of vaporization of aqueous salt solutions, *J. Phys. Chem. B,* 2009, 113, 9311-9315 sets out an equation that describes the relationship between the gas inlet temperature and the steady state temperature of the column solution:

$$[\Delta T \times C_p(T_e)] + \Delta P = \rho^v(T_e) \times \Delta H_{vap}(T_e) \text{(in units of J/m}^3\text{)} \qquad (1)$$

This equation is based on the energy balance within the column at steady state equilibrium. $C_p(T_e)$ is the specific heat of the gas flowing into the bubble column at constant pressure; $T_e$ is the steady state equilibrium temperature of the column; $\rho^v$ is the water vapour density at $T_e$; $\Delta T$ is the temperature difference between the gas entering and leaving the column; $\Delta P$, the additional correction term, is equal to the hydrostatic differential pressure between the gas inlet into the sinter and atmospheric pressure at the top of the column, which represents the work done by the gas flowing into the base of the column until it is released from the solution. $\Delta H_{vap}(T_e)$ is the enthalpy of vaporization of water in the solution at the steady state column solution temperature.

Figure 2:
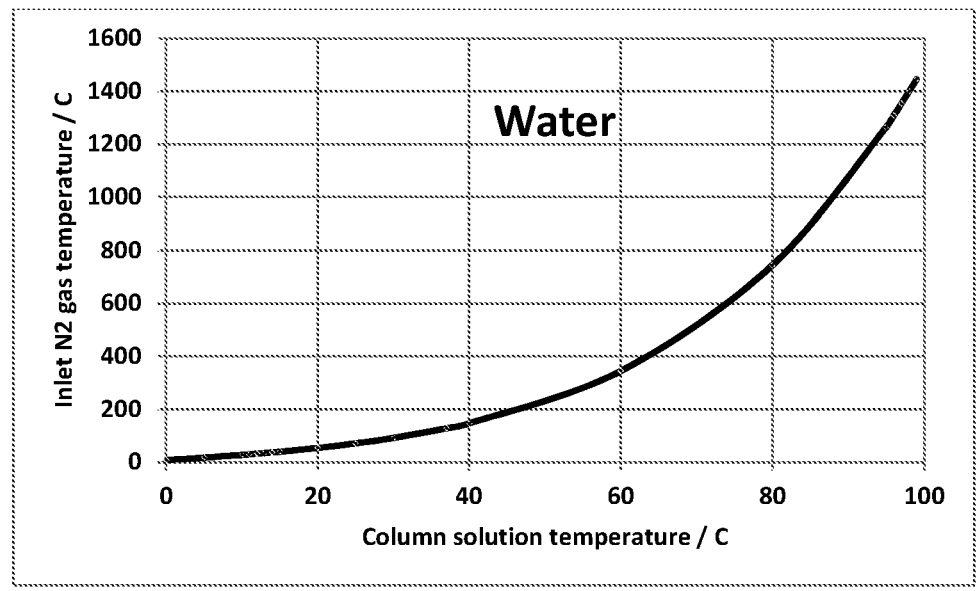
FIG. 2 is a graph of the expected temperature (° C.) of water in a column for different inlet gas ($N_2$) temperatures in a bubble column evaporator (BCE) according to equation (1).

Equation (1) describes the process by which heat is supplied from warm bubbles for vaporising water in solutions in units of Joule per unit volume. Typical results are shown in FIG. 2 for the case of heated nitrogen gas passing into a water-filled BCE. These theoretical results indicate that very hot gases can be used in a BCE, using water or an aqueous solution, without producing boiling of the water or aqueous solution.

In some embodiments, the gas in the gas bubbles has a temperature higher than the boiling point of the liquid (at the pressure to which the liquid is exposed during the method of the present invention). Accordingly, in some embodiments, the present invention provides a method for assisting a thermally induced change to a nano-sized solute or dispersed phase in a liquid, the method comprising the step of:

passing gas bubbles through the liquid, the gas in the gas bubbles having a temperature higher than the boiling point of the liquid.

The method of the invention enables the induction of thermally-induced chemical or physical changes to nano-sized solutes or dispersed phases in a liquid having a bulk temperature below that which would otherwise be required to induce the thermally-induced chemical or physical change or at which the thermally-induced chemical or physical change would proceed less rapidly. For example, using the method of the invention, the thermal decomposition of various salts can be achieved at solution temperatures where they would normally be relatively stable. Thus, the method of the invention provides many opportunities to facilitate other reactions and chemical or physical changes at reduced operating temperatures.

The gas in the gas bubbles may be any gas. The gas may, for example, be selected from the group consisting of dry air, humidified air, carbon dioxide, nitrogen, oxygen, helium or argon.

When the liquid is water or an aqueous solution, the gas when introduced into the solution preferably has a relatively low humidity, typically less than 50%, e.g. less than 40%, less than 25%, less than 20% or less than 10% relative humidity, as such a gas can more readily absorb water vapour from the liquid and will therefore result in less heating of the bulk liquid than a gas having a relatively high humidity.

The gas bubbles may be introduced into the liquid using a gas inlet having a pressure in the range of just above atmospheric pressure, e.g. in the range 1 to 1.5 atm.

When using a BCE, the gas bubbles have a certain pressure in the column of typically about 1 atm plus the hydrostatic pressure of the liquid in the column. For example, when the liquid is water or an aqueous solution, the bubbles may have, at 5-10 cm head of water, corresponding to a total pressure of about 1.005 to 1.01 atm. As they leave the column their pressure will fall to 1 atm. Dry gas bubbles entering the base of the column will rapidly absorb the vapour density of water corresponding to the temperature of the liquid in the column.

In the method of the present invention, the temperature of the gas in the gas bubbles is higher than the bulk temperature of the liquid. The temperature of the gas will be selected having regard to the desired thermally-induced chemical or physical change to the solute or dispersed phase. A person skilled in the art will be able to select the temperature of the gas effective to assist the thermally-induced chemical or physical change to the solute or dispersed phase utilising the method of the present invention having regard to the bulk temperature of the liquid and the temperature required to induce the thermally-induced chemical or physical change to the solute or dispersed phase. In some embodiments, the gas in the gas bubbles has an initial temperature of less than 600° C., e.g. less than 300° C. For example, the initial temperature of the gas in the gas bubbles may be in the range of about 25° C. to 500° C., e.g. 50° C. to 400° C., 80° C. to 300° C., 100° C. to 200° C. or about 150° C.

When the liquid is water or an aqueous solution, the temperature of the gas at the inlet though which the gas bubbles are introduced into the liquid (i.e. the temperature of the gas inlet) may be up to about 1000° C. Typically the temperature of the gas at the gas inlet is in the temperature range of about 25° C. to 600° C. In some embodiments, the temperature of the gas at the gas inlet is 50° C. to 500° C., e.g. 50° C. to 400° C., 80° C. to 300° C., 100° C. to 200° C. or about 150° C.

EXAMPLES

Various embodiments of the present invention are described below with reference to the following, non-limiting, Examples.

Materials and Method

Materials Certified reagent-grade chemicals (≥99% purity), ammonium bicarbonate ($NH_4HCO_3$), potassium persulfate ($K_2S_2O_8$) and sucrose ($C_{12}H_{22}O_{11}$) were supplied by May & Baker LTD, AnalaR and Mallinckrodt, respectively, and were used without further purification. Aqueous solutions were prepared by deionized, ultrafiltered water (Milli-Q). At room temperature, the deionized water had a conductivity <2.0 μS/cm and a natural equilibrium pH of 5.7. Reagent-grade solutions of 0.1 m NaOH were used to neutralise the hydrogen ions produced by partial decomposition of the solid $K_2S_2O_8$ during storage. All concentrations are given in molality (m) units.

Electrical Conductivity Measurements for Standard $NH_4HCO_3$ Solutions

Ammonium bicarbonate solutions were prepared in the range: 0.001 m to 2 m, with and without added sucrose (0.5-1 m). Electrical conductivity values of all the solutions were measured using a EUTECH CON 700 Conductivity Bench Meter at 25° C.

BCE System for Thermal Decomposition

Figure 3:
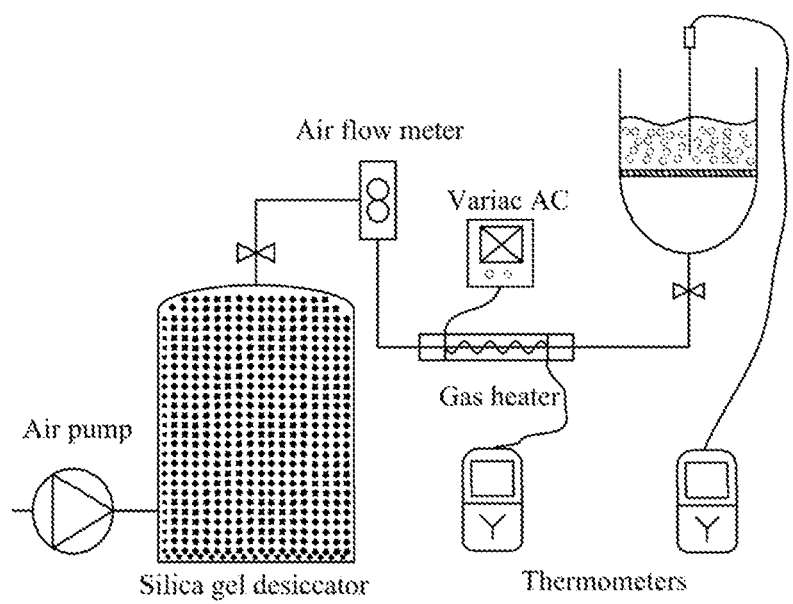
FIG. 3 shows a schematic diagram of a bubble column evaporator (BCE) for assisting a thermally-induced change to a solute or dispersed phase in a liquid.

A high air-water interface was created continuously in the bubble column with a height of 12 cm and diameter of 13 cm by passing air through a glass porous sinter (No. 2 porosity) using a HIBLOW air pump HP 120 with a maximum capacity of 120 L/min. The schematic diagram of the BCE system is shown in FIG. 3. The humidity of the air was first reduced using a large quantity of fresh silica gel (Ajax Fine Chem), and then the temperature and flow rate of the air was manipulated by a Tempco sealed inline heater and BOC air flow meter, respectively. The inlet air temperature was stably controlled using the air heater monitored by a TM-82N Tenmars thermometer with resolution of ±1.5° C. and an AC Variac electrical supply. The actual inlet temperature of the dry air flowing into the solution was measured by another Tenmars thermometer of same model, with the solution absent, just above the centre of the sinter.

Once this temperature was controlled at around 150° C. through adjusting the AC Variac supply for about 30 mins, experimental solutions were poured into the column, and then the temperature of the column solution was monitored using a thermocouple positioned at the centre of the column solution. The inlet air temperature, was maintained at 150° C. to bubble a 250 ml solution in the column, which allowed about 30 mins to stabilise the solution temperature at about 46° C., using a room temperature air flow inlet rate of 22.5 L/min, measured just prior to the heater by the flow meter. This flow rate is much less than the original rate that an air pump can produce because of the pressure in this BCE system from, say silica container and bubbling solution. However, the actual flow rate of 150° C. air pumped into the column was more than this, due to thermal air expansion. The heated air flow rate just into the solution could be calculated as:

$$\text{measured inlet air flow rate} \times \left( \frac{T_{sinter\ gas}}{T_{room}} \right)$$

with T values in Kelvin. Hence the real flow rate just into the sinter was about 32 L/min, when the flow meter indicated a value of 22.5 L/min, for an inlet air temperature of 150° C. However, the actual air flow rate within the column would only be marginally greater (by about 10%) than the room temperature air inlet flow rate because of the modest temperature increase, of up to around 46° C., which gives about 24.5 L/min for "bubble column flow" rise rate in the column solution, due to rapid water vaporization at the bubble water-air interface.

The high inlet air temperatures necessitated the use of steel and brass connectors for the down-stream output from the heater and the use of high temperature FM Insulation Rockwool as insulating material. The ammonium bicarbonate and potassium persulfate solutions were prepared at concentrations from 0.5 m to 2 m and 0.05 m, respectively. In order to ensure bubble coalescence inhibition, sucrose (0.5-1 m) was also added to some of the ammonium bicarbonate solutions. Earlier studies have shown that sucrose at this concentration does prevent bubble coalescence. For comparison, the effect of solution temperature on the decomposition of $NH_4HCO_3$ and $K_2S_2O_8$ solutions was studied over time using a Tamson model TMV 40 water bath. During these experiments, continuously stirred samples were regularly taken out from the column and water bath and their electrical conductivities and pH values were measured using a EUTECH CON 700 Conductivity meter and a pH 700 Bench meter.

1. Example 1: Thermal Decomposition of Ammonium Bicarbonate ($NH_4HCO_3$) Solutions Using the Method of the Invention As mentioned previously, the decomposition of ammonium bicarbonate ($NH_4HCO_3$) in aqueous solution is an important and energy intensive process in the application of forward osmosis and more recently in the regeneration of ion exchange resins. Using the method of the invention, the ion exchange resins comprising carboxylic acid and tertiary amine groups for desalination can be thermally regenerated at a lower energy cost than with conventional methods. In Fulks et al [Fulks, G.; Fisher, G. B.; Rahmoeller, K.; Wu, M.-C.; D'Herde, E.; Tan, J. A Review of Solid Materials as Alternative Ammonia Sources for Lean Nox Reduction with Scr; SAE Technical Paper: 2009] and Gokel et al [Gokel, G. W., Dean's Handbook of Organic Chemistry. McGraw-Hill New York: 2004; Vol. 71375937] the decomposition of ammonium bicarbonate in solution over the temperature range between 30° C. and 85° C. was reported. Complete decomposition into ammonia, carbon dioxide and water was observed above 60° C. The main decomposition reaction is described below:

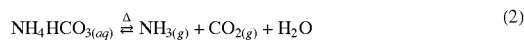

$$NH_4HCO_{3(aq)} \overset{\Delta}{\rightleftharpoons} NH_{3(g)} + CO_{2(g)} + H_2O \qquad (2)$$

The decomposition of this solute can therefore be readily measured from simple electrical conductivity measurements. The decomposition of ammonium bicarbonate using the method of the invention is described below.

Figure 4:
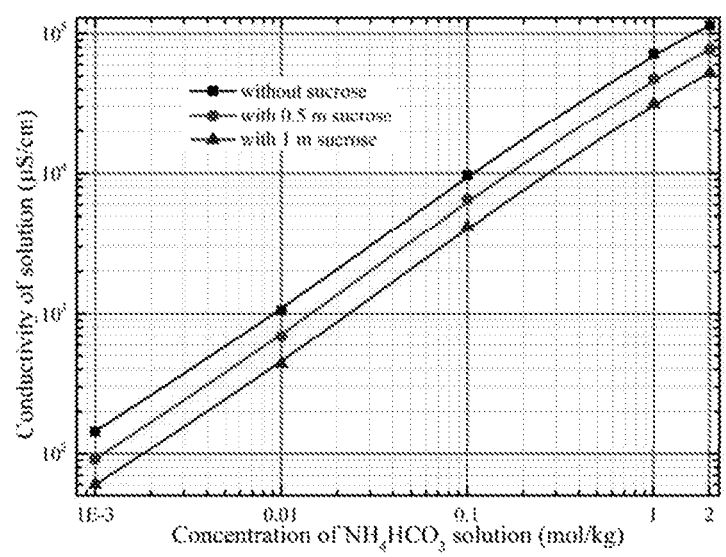
FIG. 4 is a graph of electrical conductivity for different concentrations of $NH_4HCO_3$ solution at 25° C., with and without added sucrose.

1.1 Measurement of the Electrical Conductivities of $NH_4HCO_3$ Solutions at Different Concentrations, with and without Added Sucrose Since the concentration of $NH_4^+$ and $HCO_3^-$ ions will be reduced in the aqueous solution as the $NH_4HCO_3$ salt thermally decomposes with the release of $NH_3$ and $CO_2$ gases, this process can be monitored through the measurement of the electrical conductivity of the samples taken from the bubble column. In order to determine the concentration of $NH_4HCO_3$ solutions during decomposition in the BCE, with and without added sucrose, the conductivity values of known standard solutions were measured in the range 0.001 m to 2 m at 25° C. and the results are shown in FIG. 4.

The electrical conductivity of aqueous solutions is primarily a function of the number of charge carriers in the solution, that is, the electrolyte concentration. However, ions in the solution under an applied electric field move more slowly when the solution viscosity is increased, and hence have a relatively lower electrical conductivity and vice versa. Although the dissolved sucrose in the electrolyte solution does not produce more charged ions, but increases the viscosity of the solution, producing the typical homothetic curves shown in FIG. 4. The concentrations of $NH_4HCO_3$ solution with and without added sucrose during the experimental run were determined using this data.

As hot dry bubbles enter the column, water vaporization occurs, and water vapour passes into the bubbles, which increases both the salt and sucrose concentrations. The amount of vaporised water removed, $m_v$ (g) at time t (sec), during a typical BCE process can be estimated using the following equation:

$$m_v = r_f \frac{T_c/T_f}{P_c/P_f} t \rho_v^w \qquad (3)$$

where $r_f$ (L/s) is the room temperature air flow rate, measured just prior to the heater, which was about 22.5 L/min in this study; $T_c$, $T_f$ are the air temperatures (in K) at the column solution top and at the flow meter and $P_c$, $P_f$ are the corresponding pressures at the same positions, which are the factors used to estimate the "bubble column flow" rise rate. $\rho_v^w$ is the water vapour density, in g/L, at the temperature of the solution at the top of the column, which can be calculated from the vapour pressure of the solution using the ideal gas equation.

From the initial concentration of sucrose, the actual sucrose concentration during the BCE runs can be estimated by incorporating the vaporised water correction factor and then the $NH_4HCO_3$ concentration can be determined using FIG. 4.

Using the measured concentrations of $NH_4HCO_3$ solution based on the conductivity-concentration data given in FIG. 4, the percent decomposition of $NH_4HCO_3$ at time (t) in the BCE process was calculated using the formula:

$$\text{decomposition \%} = \frac{[NH_4HCO_3]_t}{[NH_4HCO_3]_0} \times 100 \quad (4)$$

Here $[NH_4HCO_3]_t$ is the concentration value of $NH_4HCO_3$ at time (t) during the BCE operation, and $[NH_4HCO_3]_0$ presents the initial concentration value of $NH_4HCO_3$ just before pouring the solution into the bubble columns.

1.2 Decomposition of $NH_4HCO_3$ Solutions

Figure 5:
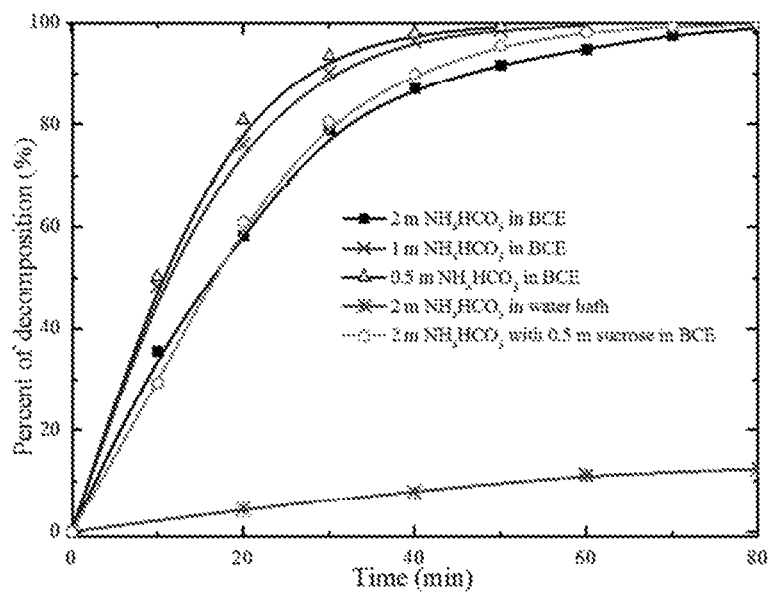
FIG. 5 is a graph of the decomposition percent of $NH_4HCO_3$ solutions over time for different concentrations of $NH_4HCO_3$ with and without sucrose in a BCE (with an inlet air temperature of 150° C. and column solution temperature of 45° C.) and in a water bath at around 45° C.

Some typical decomposition results obtained under different solution conditions are given in FIG. 5. These results clearly demonstrate that the BCE process is much more efficient for $NH_4HCO_3$ decomposition, especially compared with the standard method using a stirred water bath at the same solution temperature, of 45° C. In addition, any effects due to solution mixing in the water bath were considered by using glass rods, Teflon rods and without stirring at 45° C. The results obtained for different stirring conditions showed that the decomposition rates in the water bath remained the same, which indicates that the continuous mixing by the bubbling process in the BCE did not itself contribute to the $NH_4HCO_3$ decomposition. Furthermore, different concentrations of $NH_4HCO_3$ decomposition were also studied as shown in FIG. 5.

Figure 6:
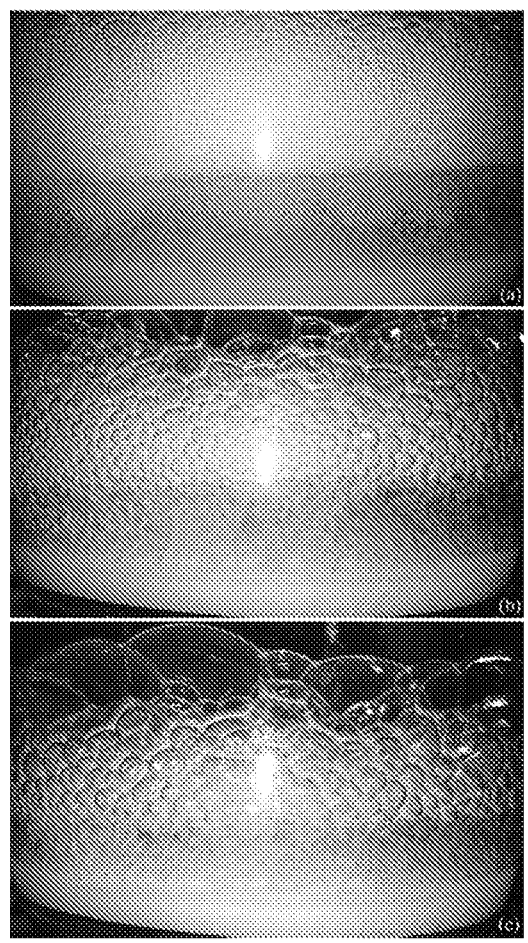
FIG. 6 shows photographs of the bubble sizes in $NH_4HCO_3$ solution with corresponding concentrations at experimental time (a) 10 min at around 1.3 m (b) 30 min at around 0.09 m and (c) 50 min at around 0.01 m.

During the experiments, it was also observed that the presence of $NH_4HCO_3$ above about 0.5 m inhibited bubble coalescence similar to 0.17 M NaCl and that fine (1-3 mm diameter) bubbles were produced within the BCE process (see FIG. 6a). Using the photos taken during the decomposition of 2 m $NH_4HCO_3$ solution, it was clear that after bubbling for 30 min the average bubbles size started to increase (see FIG. 6b) and finally after almost complete decomposition of $NH_4HCO_3$ at around 50 min, the bubbles size became the same as in pure water, providing a clear visual evidence for the complete decomposition of $NH_4HCO_3$ in the aqueous solution (see FIG. 6c). That is the thermal decomposition of ammonium bicarbonate solutions into ammonia and carbon dioxide gas and the reduction in $NH_4HCO_3$ concentration can clearly be seen by an obvious increase in bubble size.

As mentioned earlier, coalescence inhibited bubbles are of smaller average size and so increase the probability of collisions with materials dispersed or dissolved in the column solution. These smaller bubbles initially with a hot surface layer will transfer heat efficiently within the BCE, to materials dispersed or dissolved in the column solution. Therefore, maintaining the small bubble sizes throughout the BCE process, by inhibiting bubble coalescence, should enhance the decomposition efficiency. This effect was studied here using solutions with and without added sucrose. It has already been established that sucrose prevents bubble coalescence (at 0.5 m or higher) without producing any additional charged ions within the solutions [Craig, V.; Ninham, B.; Pashley, R., Effect of Electrolytes on Bubble Coalescence. *Nature* 1993, 364, 317-319]. As a result, by monitoring the electrical conductivities of the sucrose and $NH_4HCO_3$ mixed solutions with time and using the reference data in FIG. 4, the actual decomposition percentage trend of 2 m $NH_4HCO_3$ with 0.5 m sucrose was calculated and is shown in FIG. 5. Comparison of 2 m $NH_4HCO_3$ decomposition processes in a BCE, with and without sucrose, after 30 mins, showed that the decomposition efficiency in sucrose solution was slightly higher than without added sucrose. This slightly higher decomposition efficiency may be related to the sucrose effect in maintaining finer bubbles due to bubble coalescence inhibition property. However, after 30 min of the BCE process, the significant reduction in $NH_4HCO_3$ concentration produced larger bubbles in the absence of added sucrose and so the difference with the sucrose-free solution became more significant.

1.3 Effect of Initial Bubble Temperature on $NH_4HCO_3$ Decomposition in the Method of the Invention It appears that the decomposition of $NH_4HCO_3$ in aqueous solutions within a hot air BCE system occurs due to the hot surface layer initially present around the released stream of hot air bubbles. It is therefore useful to consider the likely thickness of this heated layer as a function of inlet air temperature. The maximum extent of the layer can be estimated for a given temperature, assuming that it is uniform, from the total heat available from the freshly released bubble. For example, for a 1 mm bubble we can estimate the maximum layer thickness of water heated to, say, 80° C. by the bubbles with an initial release temperature of about 150° C. (i.e. the inlet gas temperature).

This bubble layer thickness varies with bubble size (V) and the temperatures of the inlet air, the steady state column temperature and the average temperature of the heated surface film surrounding the bubbles. The maximum heated layer thickness can be calculated using the thermal energy balance equation:

$$C_p \Delta T V = C_{water} \Delta t 4\pi r^2 \rho_w z \quad (5)$$

Where $C_p$, $C_{water}$ are the air and water heat capacities, in units of $J/(m^3 \cdot K)$ and $J/(kg \cdot K)$, respectively, and $\rho_w$ is the liquid water mass density (in $kg/m^3$). $\Delta t$, $\Delta T$ are the transient temperature increase in the water layer and the temperature reduction within the cooling bubbles, in units of K, respectively.

The volume of a layer of thickness z around a bubble is given by $4\pi r^2 z$, when z is much smaller than r. Hence the cooling of the bubble by $\Delta T$ must determine the thickness z. For example, for bubbles cooling by 100° C., the maximum heated water layer thickness, heated from 20° C. to 80° C., is typically in the range of 40-80 nm, depending on bubble size and assuming that about half of the heat supplied by the cooling bubble is used for water vaporization. So ammonium bicarbonate, or other nano-sized solutes or dispersed phases, could be decomposed in this surface region, as shown in FIG. 1. When the inlet gas temperature is increased, the thickness of the surface hot water layer would also be increased, provided the mean temperature of the film and other assumptions are fixed. Consequently, the volume of the decomposition area (in the hot bubble layer) is correspondingly increased, leading directly to improved decomposition.

Figure 7:
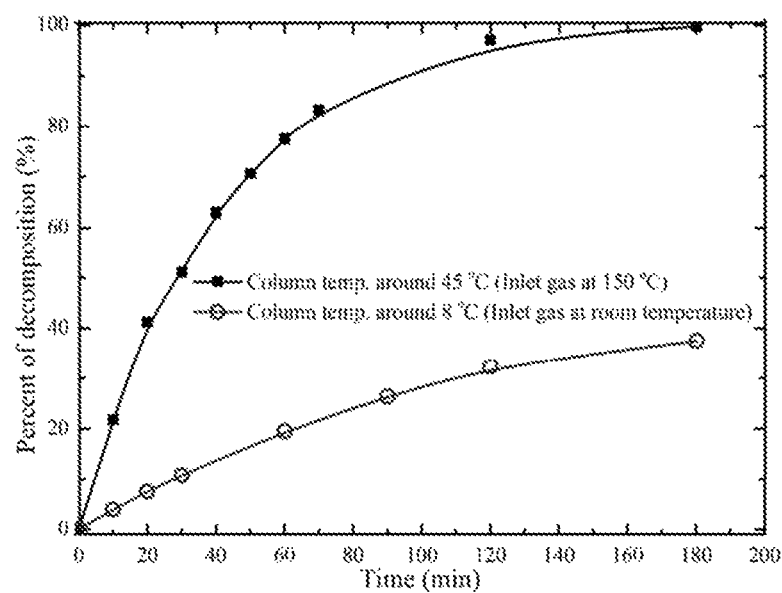
FIG. 7 is a graph of the decomposition percent over time for 2 m $NH_4HCO_3$ solution in a BCE with inlet gas (dry air) at 150° C. or at room temperature (around 22° C.).

The effect of inlet gas temperature on ammonium bicarbonate decomposition was also studied using inlet gas temperatures of 150° C. and room temperature (see FIG. 7). In order to compensate the effect of vaporised water in different temperatures, as described in Equation 5. 500 ml solutions of 2 m $NH_4HCO_3$ were used in these experiments. Typical results given in FIG. 7 show that the decomposition of 2 m $NH_4HCO_3$ solution can occur even at lower BCE solution temperatures, of say 8° C. (which is much lower than the reported solution decomposition starting temperature of around 30° C.), and has an even higher decomposition efficiency compared with water bath heating at 45° C. (see FIG. 5). It appears likely that the continuous removal of the gaseous decomposition products of $NH_4HCO_3$ solution drives the process, even at low temperatures.

2. Example 2: Thermal Decomposition of $K_2S_2O_8$ Solutions Using the Method of the Invention Potassium persulfate ($K_2S_2O_8$) in aqueous solutions is often used as a radical initiator for the process of emulsion polymerization. Persulfates are among the most powerful and useful oxidizing agents and sodium and potassium persulfate salts are mostly used. However, the persulfates decomposition generally requires high activation energy and are relatively slow at room temperature. The application of the method of the invention for persulfate decomposition could widen their applications. The thermal decomposition of the persulfate ion involves three main reactions in acidic solution, including the formation of mono-persulphuric acid ($H_2SO_5$), which further decomposes into hydrogen peroxide ($H_2O_2$) (as reported in Kolthoff et al [Kolthoff, I.; Miller, I., The Chemistry of Persulfate. I. The Kinetics and Mechanism of the Decomposition of the Persulfate Ion in Aqueous Medium J. Am. Chem. Soc. 1951, 73, 3055-3059]), as described below:

(6)

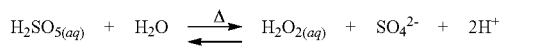
(7)

(8)

The production of acid during thermal decomposition was used in this study as a measure of the extent of decomposition of this solute in the hot gas BCE process. The application of the BCE process opens up a new approach to the thermal decomposition of degradable salts in aqueous solution. The hot surface layer on bubbles (see FIG. 1) created within the BCE plays a significant role in providing high heat and mass transfer efficiency, since the BCE is a direct contact evaporator. Degradable chemicals exposed to this hot layer can be efficiently decomposed into other products. In addition, gaseous products can be rapidly captured by the rising bubbles, due to the internal gas/vapour rotational flow within the rising bubbles, as mentioned earlier.

Figure 8:
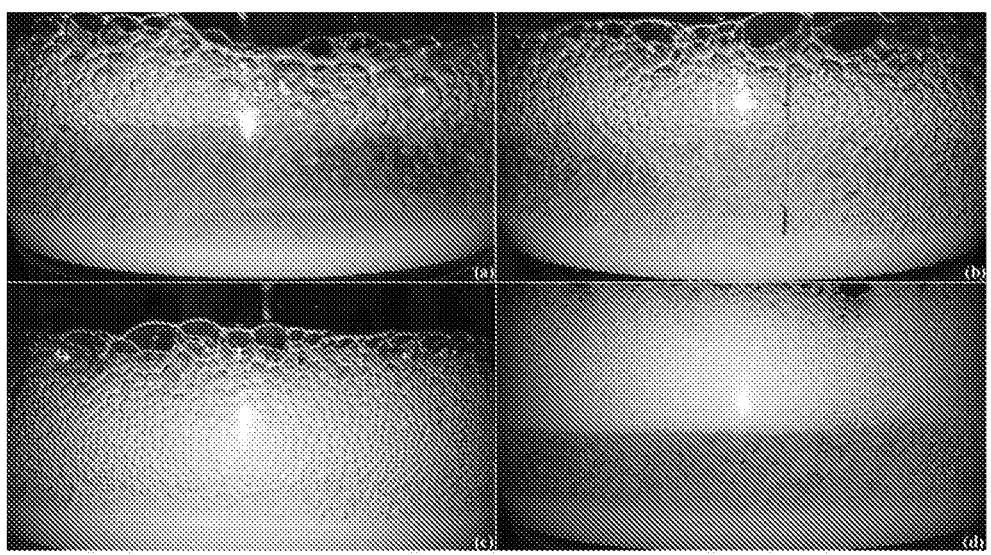
FIG. 8 shows photographs of the bubble sizes in 0.05 m $K_2S_2O_8$ solution in a BCE system (with inlet air temperatures of 150° C.) (a) at the beginning stage (b) at around 50 mins (c) at around 90 mins and (d) with added 0.5 m sucrose.

2.1 Decomposition of $K_2S_2O_8$ Solution Using the Method of the Invention In these series of experiments, 0.05 m $K_2S_2O_8$ solutions, with and without sucrose (0.5 m), were used in a BCE process with inlet dry air at 150° C. For comparison, decomposition was also studied using a continuously stirred water bath. Both the water bath and BCE solution had an operating temperature around 47° C., for direct comparison. As $K_2S_2O_8$ has a reasonably low solubility in water, of around 0.16 m, the BCE process was designed using the added sucrose in order to maintain finer bubbles and hence more efficient decomposition, as shown in FIG. 8 (d). Without adding sucrose, see FIGS. 8 (a)-(c), comparatively larger bubbles were observed. It was observed that 0.05 m solutions of $S_2O_8^{2-}$ only produce a weak bubble coalescence inhibition effect. But with increasing decomposition the higher concentration of $SO_4^{2-}$ ions produced (which would be about 0.1 m if completely decomposed) produced visibly small bubbles, as expected from earlier studies.

The concentration of hydrogen ions, as one of the main thermal decomposition products of persulfate ions, can be used as a measure of decomposition. Measured pH values were converted into the remaining concentration of $K_2S_2O_8$ in the BCE experiments based on reactions (2) and (3), and hence the decomposition percentage was calculated using the following relation:

$$\text{decomposition \%} = \frac{[H^+]_t/2}{[S_2O_8^{2-}]_0} \times 100 \qquad (9)$$

Where $[H^+]_t$ is the concentration of hydrogen ions produced during the experimental time (t) in the BCE process and $[S_2O_8^{2-}]_0$ presents the initial concentration of $K_2S_2O_8$. This analysis assumed no appreciable volume change before and after adding $K_2S_2O_8$ and sucrose into the pure water to make solutions, that is to say, assuming not much difference between molarity and molality based concentrations in this case. In addition, Equation (3) was used to estimate the concentration changes caused by water vapour evaporation in the BCE process. The negligible effect of hydrogen peroxide ($H_2O_2$) dissociation into hydrogen ions was not considered in these decomposition calculations. The results obtained are summarised in FIG. 9. The BCE process again shows much more efficient decomposition, with added 0.5 m sucrose, around 10 times as compared to that of simple heating in a stirred water bath. The use of fine bubbles in the BCE produced by the added sucrose would be expected to enhance the decomposition process, as observed. With no sucrose addition during the BCE process, much lower decomposition rates were observed, even slightly less than those measured in a water bath. It is possible that the added 0.5 m sucrose catalyses the reaction of $S_2O_8^{2-}$ with water molecules, due to perturbation of the initial water structure, and so causes a slightly enhanced decomposition rate.

2.2 an Examination of Other Factors Affecting Decomposition Efficiency

Figure 10:
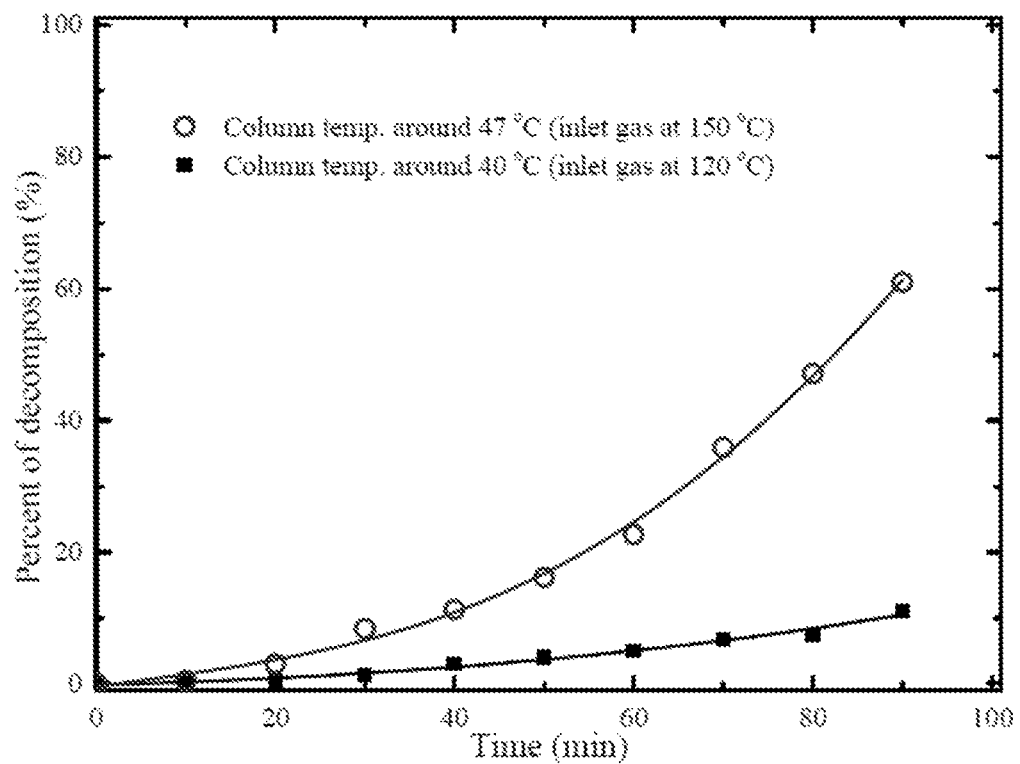
FIG. 10 is a graph of the decomposition percentage over time for 0.05 m $K_2S_2O_8$ solution with 0.5 m sucrose in a BCE system with an inlet air temperature of 150° C. or 120° C.

It is also interesting to consider other factors which might influence the efficiency of the decomposition process. Although the main factor appears to be the temperature of the inlet gas bubbles, efficient product gas removal also appears to improve decomposition rate for $NH_4HCO_3$ solutions, as shown in FIGS. 5 and 7. Similarly for $K_2S_2O_8$, higher inlet gas temperatures facilitates decomposition at much higher efficiency, more than 5 times within 90 mins and even with only a 7° C. difference in the column solution temperature, as can be seen from the results shown in FIG. 10.

Figure 11:
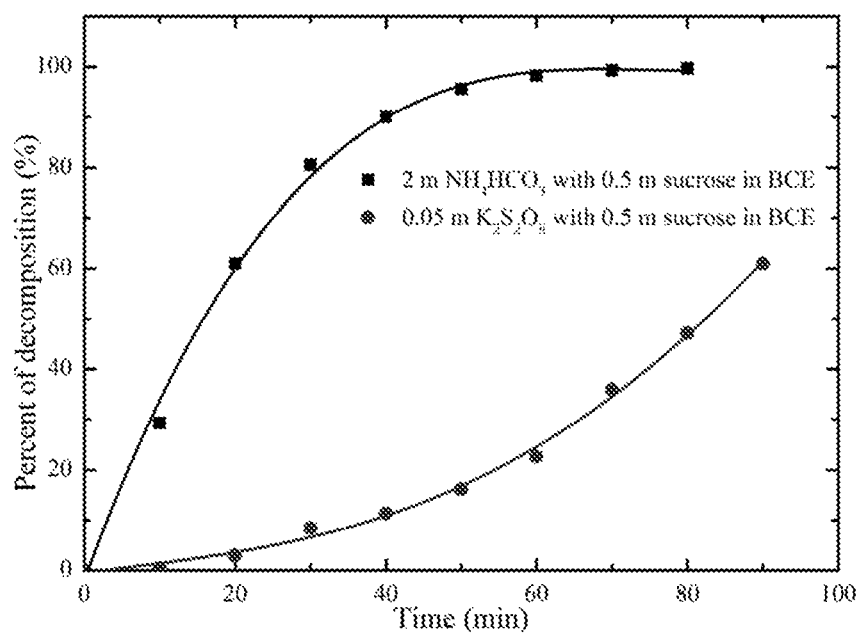
FIG. 11 is a graph of the decomposition percentage over time for 0.05 m $K_2S_2O_8$ and 2 m $NH_4HCO_3$ solution, both with added 0.5 m sucrose in a BCE system, with an inlet air temperature of 150° C.

Besides the influence of the inlet gas temperature, it is also interesting that $K_2S_2O_8$ with 0.5 m sucrose in BCE (see FIG. 9) appears to have a different type of decomposition behaviour compared with $NH_4HCO_3$, as shown in FIG. 11.

Figure 12:
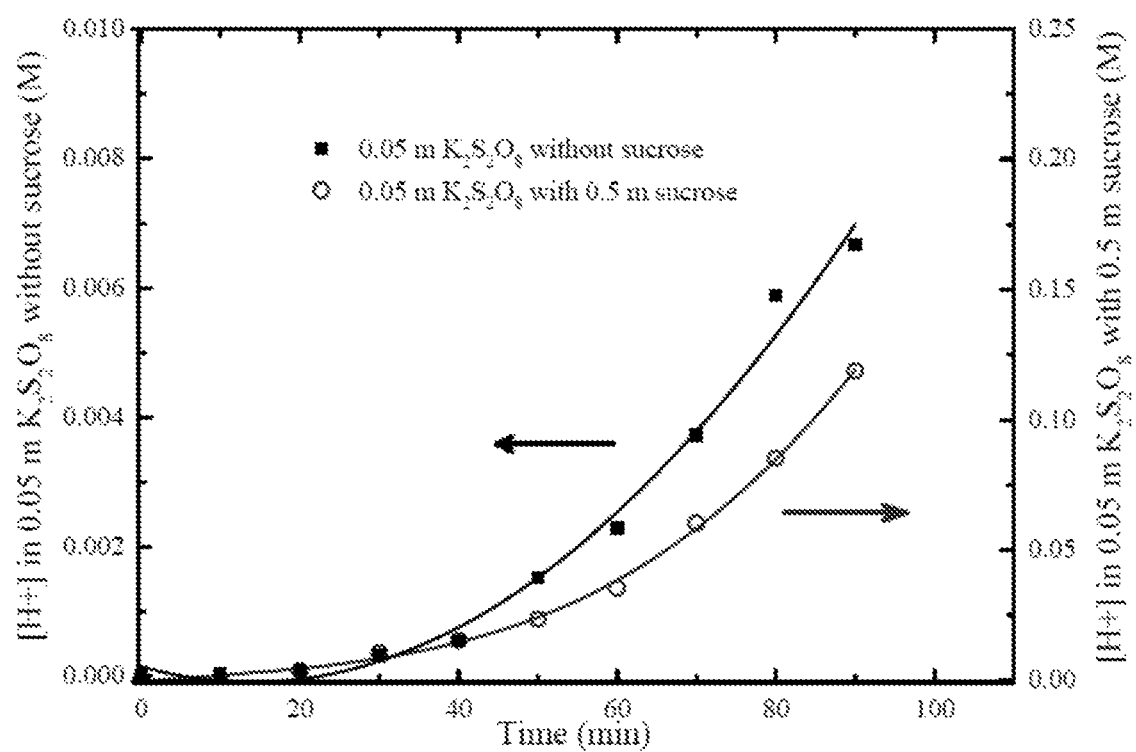
FIG. 12 is a graph of the measured hydrogen ion concentration over time for 0.05 m $K_2S_2O_8$ solution with and without sucrose, within a BCE process using an inlet air temperature of 150° C.

Clearly, in the method of the invention, $NH_4HCO_3$ behaves like a simple decomposition where the rate reduces as the concentration of reactant falls and so gives a clear plateau at high decomposition levels. By comparison, for persulfate, the situation seems to be different. This is most likely due to the fact that the acid produced catalyses the decomposition reaction and hence the rate increases as the acid builds up. The results given in FIG. 12 illustrate that the addition of sucrose has a significant effect on the persulfate ions decomposition, with more than 20 times the amount of hydrogen ions produced with added sucrose. More interestingly, the results also indicate that the decomposition rate of persulfate ions was increased with the availability of more hydrogen ions in the solution. Kolthoff et al have also reported this finding that persulfate ion decomposition is catalysed by hydrogen ions and more acidic solution enables more efficient decomposition. In addition, the results shown in FIG. 12, in 0.05 m $K_2S_2O_8$ solution (without sucrose) using an inlet gas at 150° C., the $SO_4^{2-}$ (or acid) was at a relatively low concentration even after 90 mins, of about 0.007 M, which was insufficient to prevent bubble coalescence and hence larger bubbles were observed (see FIG. 8*c*).

Figure 9:
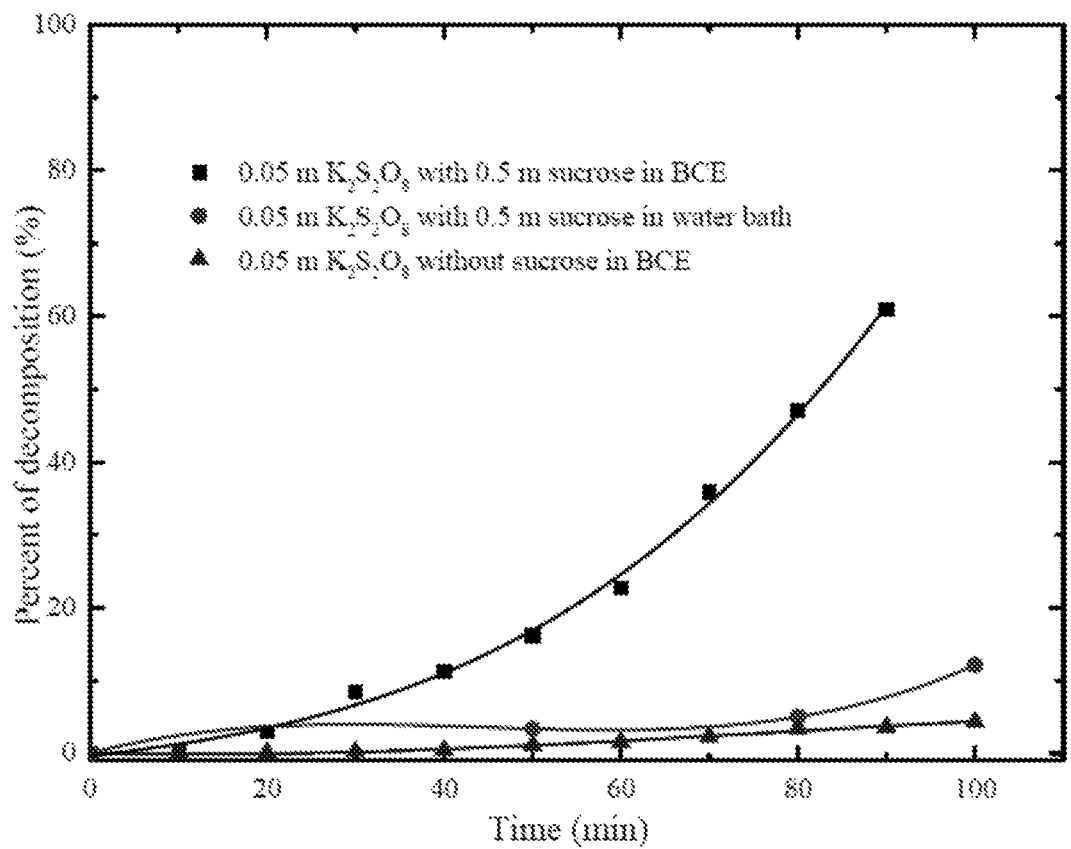
FIG. 9 is a graph which shows the comparison of the percent solution decomposition over time for 0.05 m $K_2S_2O_8$ solution in (i) a BCE process (with and without sucrose) having an inlet dry air at a temperature of 150° C. and (ii) a water bath (with added sucrose only). In both processes the bulk solution temperature is about 47° C.

The results obtained on the BCE decomposition of $K_2S_2O_8$ summarized in FIGS. 9 and 12, and the photographs of an operating bubble column in FIG. 8, clearly demonstrate that any interaction between the solute and the sinter surface in direct contact with the solution has little or no effect on the decomposition rate. This must be because the upper surface of the sinter will have a temperature close to that of the column solution with which it is in intimate contact. Hence, the substantial increase in decomposition rate on addition of sucrose must be almost entirely due to the reduction in bubble sizes and increase in the hot bubbles surface area within the column.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for assisting a thermally-induced change to a nano-sized solute or dispersed-phase in a liquid, the method comprising the step of:
    passing gas bubbles through the liquid, the gas in the gas bubbles having a temperature higher than the bulk temperature of the liquid and causing the formation of a transient hot surface layer in the liquid around the gas bubbles,
    wherein the nano-sized solute or dispersed-phase undergoes a thermally-induced change during the passing of gas bubbles through the liquid,
    wherein the thermally-induced change occurs through an interaction between the nano-sized solute or dispersed phase with the transient hot surface layer,
    wherein the thermally-induced change is one or more of:
        (i) a thermally-induced chemical change of the nano-sized solute or dispersed phase, (ii) a thermally-induced chemical reaction of the nano-sized solute or dispersed phase, and (iii) a thermal decomposition of the nano-sized solute or dispersed phase,
    wherein the liquid is water or an aqueous solution, the bubbles have a diameter of 0.1 mm to 7 mm, and the gas in the gas bubbles has a relative humidity of less than 50%.

2. The method according to claim 1, wherein the bulk temperature of the liquid is less than the temperature which would cause the thermally-induced change to the nano-sized solute or dispersed-phase.

3. The method according to claim 1, wherein the nano-sized solute or dispersed-phase has a diameter of less than 500 nm.

4. The method according to claim 3, wherein the nano-sized solute or dispersed-phase has a diameter of 0.5 nm to 200 nm.

5. The method according to claim 1, wherein the bubbles have a diameter of 1 mm to 3 mm.

6. The method according to claim 5, wherein the bubbles have a diameter of approximately 2 mm.

7. The method according to claim 1, wherein the nano-sized solute or dispersed-phase is selected from the group consisting of thermally decomposable inorganic solutes, thermally decomposable organic solutes, enzymes, antibiotics and hormones.

8. The method according to claim 7, wherein the nano-sized solute or dispersed-phase is a thermally decomposable inorganic solute.

9. The method according to claim 8, wherein the thermally decomposable inorganic solute is an ion of an inorganic salt.

10. The method according to claim 9, wherein the ion is selected from the group consisting of acetates, persulfates, ammonium, bicarbonates, carbonates and peroxides.

11. The method according to claim 9, wherein the inorganic salt is $NH_4HCO_3$ or $K_2S_2O_8$.

12. The method according to claim 7, wherein the nano-sized solute or dispersed-phase is an enzyme.

13. The method according to claim 7, wherein the nano-sized solute or dispersed-phase is an antibiotic.

14. The method according to claim 7, wherein the nano-sized solute or dispersed-phase is a hormone.

15. The method according to claim 1, wherein the liquid is an aqueous solution, and said aqueous solution comprises a bubble coalescence inhibitor.

16. The method according to claim 15, wherein the bubble coalescence inhibitor is selected from the group consisting of NaCl, $CaCl_2$, sucrose, emulsifiers and surfactants.

17. The method according to claim 16, wherein the bubble coalescence inhibitor is sucrose.

18. The method according to claim 16, wherein the bubble coalescence inhibitor is a surfactant or an emulsifier.

19. The method according to claim 1, wherein the gas in the gas bubbles is selected from the group consisting of dry air, humidified air, carbon dioxide, nitrogen, helium, argon and oxygen.

20. The method according to claim 1, wherein the gas in the gas bubbles has a temperature of less than 600° C.

21. The method according to claim 20, wherein the gas in the gas bubbles has a temperature of less than 300° C.

22. The method according to claim 1, wherein the nano-sized solute or dispersed-phase has a diameter of 0.1 nm to 250 nm.

23. The method according to claim 1, wherein the gas in the gas bubbles has a relative humidity of less than 25%.

* * * * *